United States Patent [19]

Mager et al.

[11] Patent Number: 5,677,410

[45] Date of Patent: Oct. 14, 1997

[54] CARBOSILANE-DENDRIMERS, CARBOSILANE-HYBRID MATERIALS, METHODS FOR MANUFACTURING THEM AND A METHOD FOR MANUFACTURING COATINGS FROM THE CARBOSILANE-DENDRIMERS

[75] Inventors: Michael Mager, Leverkusen; Jörg-Dietrich Jentsch, Mühlheim a.d.Ruhr; Christoph Schild, Leverkusen, all of Germany

[73] Assignee: Bayer AG, Leverkusen, Germany

[21] Appl. No.: 641,847

[22] Filed: May 2, 1996

[30] Foreign Application Priority Data

May 16, 1995 [DE] Germany .................. 195 17 839.4
Jan. 30, 1996 [DE] Germany .................. 196 03 242.3

[51] Int. Cl.$^6$ ............................................ C08G 77/06
[52] U.S. Cl. ................... 528/15; 528/19; 528/21; 556/431; 556/435; 556/459; 556/479
[58] Field of Search .................. 528/15, 19, 21; 556/479, 459, 431, 435

[56] References Cited

U.S. PATENT DOCUMENTS 5,276,110  1/1994  Zhou et al. ........................ 525/479
5,378,790  1/1995  Michalczyk et al. ................. 528/35

FOREIGN PATENT DOCUMENTS

WO 94/06807  3/1994  WIPO.

OTHER PUBLICATIONS van der Made et al., *Dendrimeric Silanes*, Advanced Materials, 1993, 5, No. 6, pp. 466–468.

Zhou et al., *Synthesis of Novel Carbosilane Dendritic Macromolecules*, Macromolecules, 1993, 26, pp. 963–968.

Seyferth et al., *Synthesis of an Organosilicon Dendrimer Containing 324 Si—H Bonds*, Organometallics, 1994, 13, pp. 2682–2690.

DIN 1520, *Paints and Varnishes; cupping test*, Feb., 1982, pp. 1–4.

*Standard Test Method for Resistance of Organic Coatings to the Effects of Rapid Deformation (Impact)*, American Society for Testing and Materials, D2794, pp. 1–2, Nov. 1993.

Rosenberg et al., *Preparation of Some Vinylsilanes with Vinylmagnesium Chloride*, J.Am.Chem.Soc., vol. 22, Oct. 1957, pp. 1200–202.

International Standard, ISO 2409, *Paints and Varnishes—Cross–cut test*, Second Edition, Aug. 15, 1992.

Beatriz Alonso et al., *Organometallic Silicon Dendrimers*, J. Chem. Soc., Chem. Commun., Aug. 1994, pp. 2575–2576.

*Standard Test Method for Film Hardness by Pencil Test*, American Society for Testing and Materials, D3363, pp. 1–2, Jan. 1993.

Lorenz et al., *Carbosilane–Based Dendritic Polyols*, Macromolecules 1995, 28, pp. 6657–6661, Aug. 1995.

John L. Speier, *Homogenous Catalysis of Hydrosilation by Transition Metals*, Advances in Organometallic Chemistry, vol. 17, pp. 407–447, 1979.

Melpolder et al., *Optimization of Sol–Gel Film Properties*, Mat.Res.Soc.Symp.Proc., vol. 121, 1988, pp. 811–816.

*Primary Examiner*—Melvyn I. Marquis
*Attorney, Agent, or Firm*—Connolly & Hutz

[57] ABSTRACT

The present invention relates to novel functional carbosilane-dendrimers, organic-inorganic carbosilane-hybrid materials, methods for manufacturing them, methods for manufacturing coatings from the functional carbosilane-dendrimers and the use thereof.

17 Claims, No Drawings

CARBOSILANE-DENDRIMERS, CARBOSILANE-HYBRID MATERIALS, METHODS FOR MANUFACTURING THEM AND A METHOD FOR MANUFACTURING COATINGS FROM THE CARBOSILANE-DENDRIMERS

The present invention relates to novel functional carbosilane-dendrimers, organic-inorganic carbosilane-hybrid materials, methods for manufacturing them, methods for manufacturing coatings from the functional carbosilane-dendrimers and the use thereof.

The term "dendrimers" is applied to highly branched molecules with a highly ordered, mostly three-dimensional structure, whose molecular weight lies in the range of those of oligomers or polymers.

Dendrimers have the advantage, however, that they can be synthesized deliberately with an exactly uniform molecular weight, whereas the conventional polymers always have a particular molecular weight distribution. In addition, particular functional dendrimers, such as those with vinyl terminal groups, can be manufactured with a defined number of such reactive groups.

The carbosilane-dendrimers known to date are synthesized starting from an initiator core by alternate hydrosilylation and Grignard reaction (U.S. Pat. No. 5,276,110, Adv. Mater. 1993, 5, 466–468, Macromolecules 1993, 26, 963–968, J. Chem. Soc., Chem. Commun. 1994, 2575–2576 und Organometallics 1994, 13, 2682–2690). For example, the initiator molecule tetravinylsilane is reacted with $HSiCl_2CH_3$ in thf under Pt catalysis. A vinylsilane is synthesized once again, by reaction with vinylmagnesium halide, and is available for further hydrosilylation.

It has been impossible to date, however, to produce high-molecular weight carbosilane-dendrimers with a defined number of functional Si—OH terminal groups.

Si—OH-functional carbosilane-dendrimers permit, however, a large number of reactions, for example bonding to metal compounds, as per Equation 1

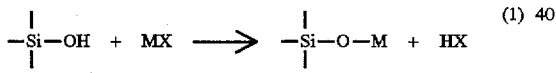

with M=metal and X=alkyl, alkoxy, halogeno or hydrido and are therefore of great interest. Thus, for example, the bonding of catalytically active metal compounds, e.g. for their immobilization or else for the manufacure of organic-inorganic hybrid materials, is extremely important. It is already known from WO 94/06807 that organic-inorganic hybrid materials can be manufactured by reacting carbosilanes containing trialkoxysilane groups with water and a catalyst or a carboxylic acid in a suitable solvent. Very thin, transparent films can be obtained crack-free by dipping suitable substrates in these solutions (dip coating). These carbosilane- dendrimers containing Si—O-alkyl terminal groups are subjected to hydrolysis slowly in the presence of humidity. Moreover, the reactivity of individual metal alkoxides to hydrolysis and condensation varies widely. Alkoxides of titanium, zirconium or aluminium react far more rapidly with water than the corresponding silicon alkoxides. Cocondensation of the above-mentioned alkoxides is very difficult, since the reactive species react with water at such a rate that they often cannot be embedded into a homogeneous network, but instead form precipitates from the corresponding metal (hydroxy) oxides. To prevent this, the concentration of water in the reaction solution must be as low as possible.

There was therefore a major requirement for Si—OH-functional carbosilane-dendrimers that can be reacted with reactive metal alkoxides without the system having in addition to contain water.

An adequate shelf-life of functional carbosilane-dendrimers is furthermore desirable for the application as a coating resin.

The object of the present invention is therefore the production of high molecular-weight functional carbosilane-dendrimers which possess a defined number of terminal Si—OH groups and can therefore be reacted without the presence of water with metal alkoxides, such as $Ti(OR)_4$, $Zr(OR)_4$, $Al(OR)_3$ or else $Si(OR)_4$, to form carbosilane-dendrimers with O-metal bonds, which during hydrolysis with water do not display the disadvantages described above of precipitate formation by metal (hydroxy) oxides and which form homogeneous networks. In addition the carbosilane-dendrimers are to have an unlimited shelf life. In addition the compounds should be simple to manufacture.

Surprisingly it has now been found that carbosilane-dendrimers containing terminal Si—OH groups, which are stabilized with alkyl and/or aryl groups, fulfil these requirements.

The present invention therefore provides functional carbosilane-dendrimers with the formula

with i=3,4 preferably i=4, n=2–6, preferably n=2 and R=alkyl and/or aryl, where n can be the same or different inside the molecule and where the other groups stand for the following a) X=OH
  with a=1 or
b) X=[$(CH_2)_nSi(OH)R_2$]
  with a=1 to 3, preferably a=3 or
c) X=[$(CH_2)_nSiR_{3-a}[(CH_2)_nSi(OH)R_2]_a$]
  with a=1–3, preferably a=3 or
d) X=[$(CH_2)_nSiR_{3-a}[(CH_2)_nSiR_{3-a}[(CH_2)_nSi(OH)R_2]_a]_a$]
  with a=1–3, preferably a=3.

The alkyl groups R in the context of the invention are preferably linear or branched, optionally substituted $C_1$-$C_5$ alkyl groups.

The term "substituted" in the context of the invention includes all common substituents, such as halogen, alkyl, amine etc.

The aryl groups R in the context of the invention are preferably optionally substituted $C_6$ rings.

When fully formulated, the carbosilane-dendrimers according to the invention correspond to formulae (Ia–d)

  (Ia)

  (Ib)

  (Ic)

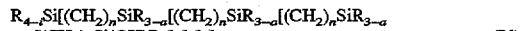  (Id)

In a preferred form of embodiment of the present invention the values of the indices n inside the molecule are the same.

Carbosilane-dendrimers with the formulae $Si[(CH_2)_2Si(OH)Me_2]_4$, $Si[(CH_2)_2Si[(CH_2)_2Si(OH)Me_2]_3]_4$ or $Si[(CH_2)_3Si(OH)Me_2]_4$, where Me is a methyl group, are particularly preferred.

The outstanding shelf-life of the carbosilane-dendrimers according to the invention is also worth noting. The colourless powders can also be stored in humid air for many months without undergoing changes. In contrast to already known carbosilane-dendrimers with functional terminal groups, such as Si-vinyl, Si—O-alkyl or Si—Cl, there is available only for the novel carbosilane-dendrimers an effective purification step which, unlike chromatographic methods, can also be performed on a commercial scale. Exceptionally pure and hence uniform carbosilane-dendrimers can be supplied in large quantities. Carbosilane-dendrimers with O-metal bonds are also obtainable from these Si—OH-functional carbosilane- dendrimers by reaction with metal alkoxides in the presence of a catalyst. In addition it has been found that the latter produce, after hydrolysis with water and crosslinking by condensation using a sol-gel process, organic-inorganic hybrid materials with outstanding properties. The latter are used as coatings for the transparent coating of surfaces. Particular mention should be made here of the high scratch-resistance combined with flexibility, transparency, good thermal stability and chemical resistance.

The present invention in addition provides a method for manufacturing the carbosilane-dendrimers according to the invention of formula (I), according to which the dendrimers of formula (II)

$$R_{4-i}[Si(CH_2)_nSiZ_cR_{3-c}]_i \qquad (II)$$

with i=3, 4, preferably i=4, n=2 to 6, preferably n=2 and R=alkyl and/or aryl, where n can be the same or different inside the molecule and where the other groups stand for the following:

a) Z=Cl, Br, I, OR
  with c=1, or
b) Z=[(CH$_2$)$_n$SiWR$_2$]
  with c=1 to 3, preferably c=3 and W stands for Cl, Br, I or OR or
c) Z=[(CH$_2$)$_n$SiR$_{3-c}$[(CH$_2$)$_n$SiWR$_2$]$_c$]
  with c=1 to 3, preferably c=3, W stands for Cl, Br, I or OR or
d) Z=[(CH$_2$)$_n$SiR$_{3-c}$[(CH$_2$)$_n$SiR$_{3-c}$[(CH$_2$)$_n$SiWR$_2$]$_c$]$_c$]
  with c=1 to 3, preferably c=3, W stands for Cl, Br, I or OR is hydrolysed in a non-polar solvent with water in the presence of a base.

Bases in the context of the invention are preferably triorganic amines, wherein the organic groups include all common alkyl, aryl and phenyl groups, linear or branched and optionally substituted, preferably trialkyl amines, particularly preferably alkyl corresponds to a $C_1$–$C_3$ group. Preferably water and also trialkyl amine are used to excess.

Preferably the method according to the invention is carried out at temperatures≧room temperature, particularly preferably at 25° to 50 ° C., more particularly preferably at 30° C. Non-polar solvents in the context of the invention are aliphatic ethers, preferably tert.-butylmethylether.

The educts can be mixed in any order. In a preferred form of embodiment of the present invention a compound of formulae (IIa–d) dissolved in a non-polar solvent is added drop-wise with stirring to a mixture consisting of base, water and non-polar solvent at temperatures≧room temperature and then stirred for at least one further hour.

The compounds of formula (IIa) can be manufactured according to conventional methods by the reaction of a suitable unsaturated silane with a hydridosilane, such as e.g. an alkoxysilane or a halogenated silane, in the presence of a catalyst, e.g. hexachloroplatinic acid in isopropanol, in a non-polar solvent.

The silanes of formula (IIa) obtained in this way can be reacted in a further step in a Grignard reaction with an alkenylmagnesium halide in aliphatic ether to obtain compounds with alkenylsilane functionality. The above-mentioned steps can be repeated to manufacture the compounds of formulae (IIb), (IIc) and (IId).

General instructions for manufacturing the compounds IIa to IId are in addition described in U.S. Pat. No. 5,276,110, Adv. Mater. 1993, 5, 466–468, Macromolecules 1993, 26, 963–968, J. Chem. Soc., Chem. Commun. 1994, 2575–2576 and Organometallics 1994, 13, 2682–2690.

Hexachloroplatinic acid and a bis [divinyltetramethylsiloxane]platinum(O) complex (Karstedt catalyst) are described in the above-mentioned literature inter alia as catalysts for the manufacture of compounds of formula (III) by the hydrosilylation of alkenylsilanes of formula (IV) with hydridosilanes of formula (V). They are used dissolved e.g. in alcohols or in xylene.

In many hydrosilylations these catalysts supply very good results as regards regioselectivity and yield, but it has been found that disadvantages are also associated with the latter. This becomes clear particularly if it is desired to convert reactions on a laboratory scale to an industrial scale.

Mention can be made here as an example of the reaction of tetra-vinylsilane with chlorodimethylsilane, as described in DE-A-19 717 839 and Organometallics 1995, 28, 6657–6661. The catalysis with hexachloroplatinic acid in isopropanol or with the Karstedt catalyst supplies the desired Si[(CH$_2$)$_2$SiClMe$_2$]$_4$ in good yield. The addition takes place regioselectively and the formation of Markoffnikov products takes place, if at all, only in insignificant amounts.

The reactions of tetravinylsilane with HSiCl$_3$, HSiCl$_2$Me or HSiClMe$_2$, in which four Si—C-bonds are linked in each case, are all strongly exothermal. As described in Macromolecules 1993, 26, 963–968, it is often necessary, even with preparations of only a few grams, to cool the reaction vessel with a cold bath, since a reflux condenser on its own can no longer recondense the low-boiling chlorosilane.

In addition to the strong development of heat it is in addition very difficult to estimate when exactly the reaction will commence. If all the educts have been purified extremely thoroughly and fresh catalyst has been prepared prior to the reaction, the reaction sometimes starts on its own without additional heating. In most cases, however, the supply of heat is required. When the reaction has started, the pre-heated mixture is then all the more difficult to control, for example by cooling. Both traces of impurities in the educts (water, HCl), and also modified catalyst activity, could be regarded as responsible for this.

In Adv. Organometallic Chem. 1979, 17, 407–409 this reaction behaviour is described as the "induction period", and is attributed to the formation of the catalytically active species itself during this "induction period".

Such an unpredictable reaction course is unsuitable for an industrial application. The rapid cooling after the start of the exothermal reaction, where it is possible at all, is so only at great expense in technical terms.

A further disadvantage of the homogeneous catalysis lies in the fact that the catalyst, even if only in small concentration, remains in the product. In addition to the fact that valuable precious metal is lost, harmful effects on subsequent products usually result from the inclusion.

It has now been found that the regioselective addition of hydfidosilanes to alkenylsilane with formation of the desired anti-Markoffnikov products takes place without the above-mentioned disadvantages and in high yield (typically about 90% (purity of the alkenylsilane used not included)), if this reaction is catalysed heterogeneously.

This heterogeneous catalyst has furthermore the advantage that partial substitution products (remaining alkenyl groups) and Markoffnikov products are either not found at all or, if they are, only in very small mounts.

It is possible with the heterogeneous catalysts used in the method according to the invention for the reaction course of the hydrosilylation and also the heat evolution to be controlled reliably by means of the catalyst content. A reduced catalyst concentration leads directly to a reduced heat evolution. Simple large-scale implementation of the method is thus possible.

In addition, the preliminary purification of the educts often becomes unnecessary through the use of the catalyst according to the invention.

A further advantage of the heterogeneous products used in the method according to the invention for an industrial application is the fact that the hydrosilylation can be conducted optionally in continuous operation, which increases the space-time yield considerably.

The separation of the supported catalyst is possible in continuous and discontinuous operation, e.g. by filtration, without any difficulty.

Products which are free from catalyst residues are obtained both in continuous and in discontinuous operation.

In addition the supported catalysts, unlike the homogeneous catalysts known according to the prior art, such as hexachloroplatinic acid in isopropanol, can be stored without loss of activity and without particular measures.

The invention therefore provides a method for manufacturing carbosilane-dendrimers of formula (III), $$R_{4-i}Si[(CH_2)_pSiZ_eR_{3-e}]_i \qquad (III)$$

with p=2–10, e=1–3, i=3,4 and R=alkyl and/or aryl, where p can be the same or different, preferably the same, inside the molecule, and where the other groups stand for the following:

Z=halogen, OR, preferably Z=Cl or b) $Z=[(CH_2)_pSiW_eR_{3-e}]$ with W=halogen, OR, preferably W=Cl, or c) $Z=[(CH_2)_pSiR_{3-e}[(CH_2)_pSiW_eR_{3-e}]_e]$ with W=halogen, OR, preferably W=Cl, characterised in that alkenylsilanes of formula (IV)

$$R_{4-i}Si[(CH_2)_{p-2}Q]_i$$

with p=2–10, i=3,4, R=Alkyl and/or aryl and a) $Q=C_2H_3$ or b) $Q=[(CH_2)_pSi(C_2H_3)_eR_{3-e}]$ with e=1–3 or c) $Q=[(CH_2)_pSiR_{3-e}[(CH_2)_pSi(C_2H_3)_eR_{3-e}]_e]$ with e=1–3 are reacted with hydridosilanes of formula (V)

$$HSiP_eR_{3-e}$$

with e=1–3, P=halogen, OR, preferably P=Cl, and R=alkyl and/or aryl in the presence of heterogeneous catalysts.

Tetravinylsilane is preferably used as the alkenylsilane and $HSiCl_3$, $HSiCl_2Me$ or $HSiClMe_2$, where Me is a methyl group, as the hydridosilane.

Tetravinylsilane and $HSiClMe_2$ are particularly preferably used.

The heterogeneous catalyst consists preferably of platinum or a platinum compound, which can be applied to a wide range of support materials. Substances based on carbon or metal oxides or metal oxide mixtures may be mentioned as examples of support materials. The support materials can be of synthetic or natural origin, i.e. consist for example of clay minerals, pumice, kaolin, bleaching earths, bauxite, bentonite, kieselguhr, asbestos or zeolite. In a preferred form of embodiment of the invention the catalytically active component is used applied to a carbon-containing support such as activated carbon, carbon black, graphite or coke, wherein activated carbon is preferred.

The supported catalyst can be used both in powder form and in lumps, e.g. as balls, cylinders, rods, hollow cylinders or rings.

The catalyst used in the method according to the invention is preferably applied to a suitable support. Its reactive component consists, preferably when in the reactive state, of a platinum halide or of a complex compound containing a platinum halide, which can in addition contain for example olefins, amines, phosphines, nitriles, carbon monoxide or water, such as $A_2Pthal_6$, where A stands for example for H, Li, Na, K, $NH_4$, Rb, Cs, $NR_4$ with R: organic group $C_6$- to $C_{10}$-aryl-, $C_7$- to $C_{12}$-aralkyl- and/or $C_1$- to $C_{20}$-alkyl group, and hal for a halogen, for example F, Cl, Br, I. Complex platinum compounds of this kind containing halogen are known in principle.

In a preferred form of embodiment of the invention the catalyst used in the method according to the invention is generated in situ. For this the platinum halide or the complex compound containing the platinum halide is produced in situ on the support during the preparation stage from a suitable halogen-free metal platinum compound and a halide-containing compound. Platinum nitrate, platinum oxide, platinum hydroxide, platinum acetylacetonate and other compounds familar to the skilled man are for example considered as halogen-free metal platinum compounds. Halogen-containing salts and complex compounds of the elements of the first to third main group and the first to eighth subgroup of the periodic table of the elements (Mendeleev) and of the rare earth metals (atomic numbers 58–71) are considered as halide-containing compounds. $NaBr$, $NaCl$, $MgBr_2$, $AlCl_3$, $NaPF_6$, $MnCl_2$, $CoBr_2$, $CeCl_3$, $SmI_2$, $CuCl_2$, $Na_2ZnCl_4$, $TiCl_4$ are examples.

The amount of the platinum halide or that of the complex compound containing the platinum halide in the reactive state preferably comes to 0.01 to 15 wt %, particularly preferably 0.05 to 10 wt %, calculated as platinum metal and referred to the total weight of the catalyst.

The following are mentioned e.g. as preferred solvents for the manufacture of supported catalysts according to the invention: water, aliphatic hydrocarbons, such as pentane, n-hexane, cyclohexane etc., aliphatic halogenated hydrocarbons, such as dichloromethane, trichloromethane, etc., aromatic hydrocarbons, such as benzene, toluene, xylene etc., halogenated aromatic hydrocarbons, such as chlorobenzene, dichlorobenzene, etc., primary, secondary or tertiary alcohols, such as methanol, ethanol, n-propanol, isopropanol, n-butanol, isobutanol, t-butanol, cumyl alcohol, iso-amyl alcohol, diethylene glycol, etc., ketones, such as acetone, 2-butanone, methyl isobutyl ketone, acetylacetone etc., ethers, such as diethylether, diisopropylether, methyl-t-butylether, dioxane, tetrahydrofuran, etc., esters, such as methyl acetate, ethyl acetate, etc., nitriles, such as acetonitrile, benzonitrile, etc., carbonates, such as dimethyl carbonate, diethyl carbonate, diphenyl carbonate, etc., dimethyl acetamide, N-methylpyrrolidinone and tetramethyl urea. Mixtures of such solvents can naturally also be used.

The manufacture of a catalyst to be used according to the invention takes place according to methods that in principle are known to the skilled man. Thus platinum-containing solutions and the above-mentioned halide-containing compounds can be precipitated on the catalyst support to be used according to the invention by soaking, adsorption, immersion, spraying, impregnation and ion exchange. It is also possible to fix platinum and the above-mentioned halide-containing compounds to the support with a base. NaOH, $Li_2CO_3$ and potassium phenolate are considered as bases. Platinum and the halide-containing compound can be applied to the support either successively in any order or simultaneously.

In the case of the application of the platinum by soaking with a platinum-containing solution the period of soaking depends to a certain extent on the platinum compound used, the form and porosity of the support used and the solvent. The latter comes preferably to a few minutes to some hours, for example 0.01 to 30 h, particularly preferably 0.05 to 20 h, more particularly preferably 0.1 to 15 h.

The mixture can be stirred during the soaking. It may also be advantageous, however, to allow the mixture to stand or to shake it, so that any moulds used are not damaged by a stirrer.

After the soaking the supported catalyst should be separated, e.g. by filtration, sedimentation or centrifuging. Surplus solvent can be separated by distillation at the same time.

After the soaking the supported catalysts so obtained are dried. This can take place in the air, under vacuum or in a gas current. Suitable gases for the drying of the supported catalyst in a gas current are e.g. nitrogen, oxygen, carbon dioxide or noble gases, as well as any mixtures of the above-mentioned gases, preferably e.g. air. The drying preferably takes place at 20° to 200° C., particularly preferably at 40° to 180° C., more particularly preferably at 60° to 150° C.

The drying depends e.g. on the porosity of the support used and on the solvent used. It comes preferably to a few hours, for example 0.5 to 50 h, particularly preferably 1 to 40 h, more particularly preferably 1 to 30 h.

After the drying the dried supported catalysts can be calcined. This can take place in the air, under a vacuum or in a gas current. Suitable gases for the calcination of the supported catalyst in a gas current are e.g. nitrogen, oxygen, carbon dioxide or noble gases, as well as any mixtures of the above-mentioned gases, preferably e.g. air. The calcination preferably takes place at 100° to 800° C., particularly preferably at 100° to 700° C., more particularly preferably at 100° to 600° C.

The calcination time preferably comes to a few hours, for example 0.5 to 50 h, preferably 1 to 40 h, particularly preferably 1 to 30 h.

The supported catalysts can be used as powders or mouldings and be separated from the reaction mixture e.g. by filtration, sedimentation or centrifuging.

The present invention also provides for organic-inorganic hybrid materials that are obtainable by the reacting of the carbosilane-dendrimers according to the invention according to formula I $$R_{4-i}Si[(CH_2)_nSiX_aR_{3-a}]_i \quad (I)$$

with i=3,4, preferably i=4, n=2–6, preferably n=2 and R=alkyl and/or aryl, where n can be the same or different inside the molecule and where the other groups stand for the following a) X=OH with a=1 or b) $X=[(CH_2)_nSi(OH)R_2]$ with a=1 to 3, preferably a=3 or c) $X=[(CH_2)_nSiR_{3-a}[(CH_2)_nSi(OH)R_2]_a]$ with a=1–3, preferably a=3, or d) $X=[(CH_2)_nSiR_{3-a}[(CH_2)_nSiR_{3-a}[(CH_2)_nSi(OH)R_2]_a]_a]$ with a=1–3, preferably a=3, with metal alkoxides of the formula $$M(OR')_x$$

with M=Si, Ge, Sn, B, Al, Ga, In, Ti, Zr, Hf, V, Nb or Ta, R'=an unbranched or branched $C_1$–$C_5$ alkyl group and x stands for 3 or 4 depending on the oxidation number of M, with water and in the presence of a catalyst.

The alkyl groups R in the context of the invention are preferably linear or branched, optionally substituted $C_1$–$C_5$ alkyl groups.

The aryl groups in the context of the invention are preferably optionally substituted $C_6$ rings.

In a preferred form of embodiment of the present invention the values for the indices n inside the molecule are the same. Particularly preferably n=2 and i=4.

In a preferred form of embodiment of the present invention M=Si, Al, Ti or Zr, R' is an unbranched or branched alkyl residue and x, depending on the oxidation number of M, is 3 or 4.

Particularly preferably the metal alkoxide corresponds to the formula $Si(OEt)_4$, where Et is an ethyl group.

Catalysts in the context of the invention are inorganic or organic acids, preferably organic acids or organometallic compounds, such as e.g. zinc octoate.

The concentration of the catalyst in the total mixture preferably comes to 0.1 to 5 mol/l, particularly preferably 0.1 to 1.0 mol/l.

In a preferred form of embodiment of the present invention the reacting of the functional carbosilane-dendrimers of Formulae Ia to Id with the metal alkoxide takes place in the presence of a catalyst in a solvent.

The ratio of carbosilane-dendrimers to metal alkoxide is determined by the number of silanol groups. 1 to 4 mol, preferably one mole, of the metal alkoxide can be used per mole of silanol group.

The present invention provides in addition a method for manufacturing coatings, characterised in that carbosilane-dendrimers of formula (I)

$$R_{4-i}Si[(CH_2)_nSiX_aR_{3-a}]_i \quad (I)$$

with i=3,4, preferably i=4, n=2–6, preferably n=2 and R=alkyl and/or aryl, where n can be the same or different inside the molecule and where the other groups stand for the following a) X=OH with a=1 or b) $X=[(CH_2)_nSi(OH)R_2]$ with a=1 to 3, preferably a=3 or c) $X=[(CH_2)_nSiR_{3-a}[(CH_2)_nSi(OH)R_2]_a]$ with a=1–3, preferably a=3 or d) $X=[(CH_2)_nSiR_{3-a}[(CH_2)_nSiR_{3-a}[(CH_2)_nSi(OH)R_2]_a]_a]$ with a=1–3, preferably a=3, are reacted with metal alkoxides of formula $$M(OR')_x$$

with M=Si, Ge, Sn, B, Al, Ga, In, Ti, Zr, Hf, V, Nb or Ta, particularly preferably Si, Al, Ti, R'=an unbranched or branched $C_1$–$C_5$ alkyl group and x, depending on the oxidation number of M, stands for 3 or 4, with water and in the presence of a catalyst in a solvent.

The alkyl groups R in the context of the invention are preferably linear or branched, optionally substituted $C_1$-$C_5$ alkyl groups.

The aryl groups in the context of the invention are preferably optionally substituted $C_6$ rings.

In a further preferred form of embodiment of the present invention the values of the indices n inside the molecule are the same. Particularly preferably n=2 and i=4.

In a preferred form of embodiment of the present invention M=Si, Al, Ti or Zr, R' is an unbranched or branched alkyl group and x, depending on the oxidation number of M, is 3 or 4.

Particularly preferably the metal alkoxide corresponds to the formula $Si(OEt)_4$, where Et is an ethyl group.

Catalysts in the context of the invention are preferably inorganic or organic acids, preferably organic acids or organometallic compounds, such as e.g. zinc octoate.

The concentration of the catalyst in the total mixture preferably comes to 0.1 to 5 mol/l, particularly preferably 0.1 to 1.0 mol/l.

In a preferred form of embodiment of the present invention the reacting of the functional carbosilane-dendrimers of Formulae Ia to Id with the metal alkoxide takes place in the presence of a catalyst in a solvent.

The solvent not only ensures a homogeneous solution, but can also influence the reaction rate to a considerable extent. The gel formation should be sufficiently slow for the coating solution to be able to be worked for a few hours. Solvents in the context of the invention are e.g. alcohols. Aqueous alcohols are preferred. Ethanol or isopropanol with a water content of 5 to 25%, preferably 20%, may be mentioned as particularly preferred.

The ratio of carbosilane-dendrimer to metal alkoxide is determined by the number of silanol groups. 1 to 4 mol, preferably one mole, of the metal alkoxide can be used per mole of silanol group.

The method according to the invention is preferably carried out so that the carbosilane-dendrimer according to one of formulae Ia to Id is dissolved or suspended in the suitable mount of aqueous alcohol and mixed with the metal alkoxide. The catalyst is then added, whereupon an optionally present suspension becomes homogeneous in a few minutes. It can be ascertained by spreading a drop of the coating solution on a microscope slide if the viscosity is high enough for good processing.

The present invention in addition provides the use of the Si—OH-functional carbosilane-dendrimers according to the invention as supports for the bonding of catalytically active metal compounds.

The present invention also provides the use of the functional carbosilane-dendrimers with O-metal bond as coatings.

The coating can be applied to a wide range of surfaces by the conventional methods. For example it can be applied by means of a knife or by dipping (dip coating) in the coating solution, which results in very thin layers (a few μm).

The coating solution applied to the surface is preferably cured in the air at a suitable temperature.

Before a forced drying takes place at higher temperature, the bulk of the volatile components are preferably evaporated at room temperature.

Suitable temperatures for the curing of the coating films lie in the temperature range from 15° C. to 250° C. In the case of wet film thicknesses of 120 μm and more, complete curing at room temperature is obtained only after a few days. A temperature range of 50° C. to 120° C., which guarantees curing in a few hours, is preferred here.

The properties will be described in detail below for a coating consisting of $Si[(CH_2)_2Si(OH)Me_2]_4$ and $Si(OEt)_4$ (1:4).

The coating films produced in this way are absolutely transparent and have a high gloss. The absorbance is less than 0.002 in the range from 360 to 560 nm and about 0.03 in the range from 560 to 810 nm.

Determination of the scratch resistance by means of pencil hardness to ASTM 3363 shows that a 27 μm film on a glass surface, which has been cured at 20° C. for 24 h, cannot be scratched by a pencil with a hardness of 5H. The same result is obtained for a similarly coated steel plate.

The adhesion of the coatings was tested to ISO 2409. The best possible classification "O" was obtained both on glass and on steel, iron, aluminium or silicon.

The solvent resistance was tested by vigorous, five-minute rubbing of the coating with a cotton-wool ball soaked in solvent. The coating was not modified in any way by any of the solvents used, namely ethanol, acetone, dimethyl formamide, toluene, chloroform or n-butylacetate.

Thermogravimetric analysis (TGA) in air shows no decrease in weight up to 210° C., i.e. the film is thermally stable up to this temperature at least for a short time. Above 210° C. a weight decrease of approx. 10% is observed, which stems mainly from escaping solvent or post-curing. Only between 230° C. and 450° C. does decomposition (oxidation) of the organic component take place.

TGA under nitrogen shows that a weight decrease of approx. 4% occurs up to 235° C., compared with only approx. 3% between 235° C. und 490° C. This weight decrease can be attributed only to components which are included in the coating (e.g. solvents) or are formed at this temperature by post-curing. It is remarkable that the film can at least for a short time even be thermally stressed up to 490° C. without decomposing. Above 490° C. the organic component in the coating is broken down.

Also surprising is the surface tension of 28.5 mN/m determined from contact angle measurements, wherein the non-polar portion comes to 25.0 mN/m and the polar portion to 3.4 mN/m. The non-polar portion predominates strongly, which is unusual for a system containing many siloxane and silanol groups. The carbosilane skeleton consequently has a great influence on these parameters.

The coefficient of thermal expansion is also surprisingly high at $63 \times 10^{-6}$/K. Conventional gels produce, even where silanes with a high organic content, such as n-octyl groups, are used, coefficients of expansion in the range of only 1 to $22 \times 10^{-6}$/K, as described in Mat. Res. Symp. Proc. 1988, 121, 811–816.

The expansion coefficient determined for the coating according to the invention agrees very closely with that of e.g. polycarbonate (about $60 \times 10^{-6}$/K). It follows from the surface tension that the wetting of plastics materials should also prove satisfactory.

Mechanical testing of a coating applied to an iron slab produces a value of 11 mm for a slow deformation (indentation test to ISO 1520). This excellent value is evidence of the elasticity of the coating.

With rapid deformation (ball impact to ASTM D 2794–93) a value of 20 inch-pound is obtained.

The method according to the invention will be explained in detail by means of the following examples.

The invention is not however limited to the examples.

EXAMPLES

Preliminary remarks:

All reactions were carried out with the use of Schlenk technique under argon or in a vacuum. All the solvents used were dried prior to use by the conventional laboratory methods and used distilled under argon. Commercial educts were not subjected to further purification.

$^1$H-NMR spectra were recorded at 400 and 500 MHz, proton-decoupled $^{13}$C spectra at 100 MHz with the AMX 500 of the company Bruker. The spectrometer XR 300 of the company Varian was used at 60 MHz for the recording of the proton-decoupled $^{29}$Si spectra. The mass spectra were in the case of Maldi measurements obtained with Kratos Maldi 3 of the company Shimatzu and in the case of CI measurements with MAT 800/230 of the company Finnigan.

Commercial educts such as chlorodimethylsilane and tetravinylsilane were used without further purification. The purity of the tetravinylsilane used came to 96%.

The synthesis of $Si[(CH_2)_2Si[(CH_2)_2Si(C_2H_3)_3]_3]_4$ was carried out as described in Organometallics 1994, 13, 2682.

The synthesis of phenyltrivinylsilane from phenyltrichlorosilane and vinylmagnesium chloride was carried out as described in J. Org. Chem. 1957, 22, 1200–1202.

A 0.1% solution of hexachloroplatinic acid in absolute isopropanol was used as the hydrosilylation catalyst.

Example 1

Synthesis of $Si[(CH_2)_2SiClMe_2]_4$ 5 drops of the platinum catalyst were added at room temperature to a mixture of 5 g (36.7 mmol) of tetravinylsilane, 20.8 g (220.1 mmol) of chlorodimethylsilane and 20 ml of thf. The whole was stirred initially for 30 min at room temperature and heated to 45° C. to 50° C. A violent exothermal reaction occurred after a few minutes, the heating bath having to be removed in certain circumstances. When the temperature dropped, heating to 45° C. to 50° C. for a further 2 h took place. After cooling to room temperature stirring took place for a further 20 h and all volatile components were removed under vacuum. The product was obtained as a colourless wax.

NMR: (CDCl$_3$)

$^1$H: $\delta$=0.42 ppm (s, 6H, SiCH$_3$); 0,59 ppm and 0.68 ppm (m, 2H in each case, SiCH$_2$).

$^{13}$C{$^1$H}: $\delta$=0.93 ppm (s, SiCH$_3$); 2.06 ppm (s, SiCH$_2$); 11.26 ppm (s, ClSiCH$_2$).

Example 2

Synthesis of $Si[(CH_2)_2Si[(CH_2)_2SiClMe_2]_3]_4$ 5 drops of the platinum catalyst were added to the reaction mixture consisting of 3 g (5.20 mmol) of $Si[(CH_2)_2Si(C_2H_3)_3]_4$, 7.8 g of chlorodimethylsilane and 20 of thf and the whole was stirred initially for 30 min at room temperature. Heating to 45° C. to 50° C. then took place; the reaction that started after a few minutes was far less exothermal than that described in Example 1. Further heating to 45° C. for 2 h, followed by renewed cooling to room temperature and stirring for a further 20 h, then took place. After removal of the volatile components under vacuum, the product was obtained as a colourless solid.

Elemental analysis (C, H):

|  | C | H |
| --- | --- | --- |
| Calcd.: | 39.28% | 8.00% |
| Found: | 40.0% | 8.0% |

$C_{56}H_{136}Cl_{12}Si_{17}$
M=1712.580 g/mol

NMR: (CDCl$_3$)

$^1$H: $\delta$=0.39 ppm (s, 22H, Si(CH$_3$)$_2$ and Si(CH$_2$)$_2$Si); 0.60 ppm (m, 12H, Si(CH$_2$)$_2$SiCl).

$^{13}$C{$^1$H}: $\delta$=1.00 ppm (s, SiCH$_3$); 1.97 ppm, 2.29 ppm and 2.82 ppm (s, SiCH$_2$); 11.47 ppm (s, ClSiCH$_2$).

Example 3

Synthesis of $Si[(CH_2)_2Si(OH)Me_2]_4$

A solution of 10.0 g (19.5 mmol) of $Si[(CH_2)_2SiClMe_2]_4$ from Example 1 in 20 ml of diethyl ether was added drop-wise within 30 minutes to 8.5 g (84.0 mmol) of triethylamine and 1.62 g (90.0 mmol) of water in 300 ml of diethylether. The triethylamine hydrochloride formed was obtained as a white precipitate. After the addition, stirring took place for a further hour and the solid was then filtered off. The filtrate was freed of the solvent in a vacuum. The colourless solid so obtained was dissolved in tiff and dripped slowly into 500 ml of hexane with vigorous stirring. The product was obtained as a free, white precipitate, which did not have to be purified further after filtering off and a single washing with hexane.

A stable solid was obtained.

Melting point: 144° C.

Elemental analysis:

|  | C | H | O | Si |
| --- | --- | --- | --- | --- |
| Calcd.: | 43.58% | 10.06% | 14.51% | 31.85% |
| Found: | 43.6% | 10.1% | 14.2% | 32.1% (diff.) |

$C_{16}H_{44}O_4Si_5$
M=440.951 g/mol

NMR: (dmso-d$_6$)

$^1$H: $\delta$=0.0 ppm (s, 6H, SiCH$_3$); 0.39 ppm (m, 4H, Si(CH$_2$)$_2$Si); 5.21 ppm (s, 1H, SiOH).

$^{13}$C{$^1$H}: $\delta$=−0.63 ppm (s, SiCH$_3$); 1.93 ppm (s, Si(CH$_2$)$_4$); 9.77 ppm (s, Si(OH)CH$_2$).

$^{29}$Si{$^1$H}: $\delta$=14.26 ppm (s, Si(CH$_2$)$_4$); 16.33 ppm (s, SiOH).

MS: (CI)

m/e=337 $(Si[(CH_2)_2Si(OH)Me_2]_3^+)$

IR: (Nujol trituration)

3160 cm$^{-1}$, very broad (vO—H).

Example 4

Synthesis of $Si[(CH_2)_2Si[(CH_2)_2Si(OH)Me_2]_3]_4$ 4 g (2.34 mmol) of $Si[(CH_2)_2Si[(CH_2)_2SiClMe_2]_3]_4$ from Example 2 in 40 ml of diethyl ether were added drop-wise within 30 min to a mixture of 20.7 g (30.4 mmol) of triethylamine, 3.65 g (32.7 mmol) of water and 700 ml of diethyl ether. On completion of the addition, the reaction mixture was stirred for a further hour and the precipitate of triethylamine hydrochloride was then filtered off. The filtrate was freed of volatile components in a vacuum and the partly crystalline colourless residue was dissolved in thf. This solution was dripped into 300 ml of hexane. The product was obtained in this way as a colourless precipitate. When the latter became oily on standing, the solvent was decanted off and the oily product stirred with some diethyl ether. The after-purified finely crystalline product was filtered off and dried in a vacuum.

A stable solid was obtained.
Elemental analysis (C, H):

|  | C | H |
|---|---|---|
| Calcd.: | 45.10% | 10.00% |
| Found: | 44.8% | 9.7% |

$C_{56}H_{148}O_{12}Si_{17}$
M=1491.239 g/mol
NMR: (dmso-$d_6$)

$^1$H: δ=0.06 ppm (s, 18H, SiCH$_3$); 0.46 ppm (m, 16H, SiCH$_2$); 5.31 ppm (s, 3H, SiOH).

$^{13}$C{$^1$H}: δ=−0.42 ppm (s, SiCH$_3$); 1.89 ppm (s, Si(OH)CH$_2$CH$_2$Si); 2.23 ppm and 2.43 ppm (s, Si(CH$_2$)$_2$Si), 9.99 ppm (s, Si(OH)CH$_2$CH$_2$Si).

Example 5

Synthesis of $C_6H_5Si[(CH_2)_2SiClMe_2]_3$ 25.0 g (264.5 mmol) of chlorodimethylsilane and some drops of the Pt catalyst were added to 12.3 g (66.1 mmol) of phenyltrivinylsilane in 50 ml of thf. The reaction mixture was heated to 45–50° C. for 20 h, then cooled to room temperature, and all volatile components were removed in a vacuum. A colourless oil was obtained, which was reacted further according to Example 6 without further purification.

Example 6

Synthesis of $C_6H_5Si[(CH_2)_2Si(OH)Me_2]_3$ 26.9 g (57.4 mmol) of $C_6H_5Si[(CH_2)_2SiClMe_2]_3$ from Example 5 in 30 ml of diethyl ether were added drop-wise within 2 h to a solution of 34.5 ml (247.7 mmol) of triethylamine and 4.8 ml (264.9 mmol) of water in 1.2 l of tert.-butylmethylether. After the addition, stirring took place for a further hour at room temperature and the white precipitate of triethylamine hydrochloride was then filtered off. The colourless filtrate was freed of volatile components on a rotary evaporator. The white solid so obtained was dissolved in 30 ml of thf and dripped into 400 ml of hexane with stirring. The product was obtained as a fine white precipitate. The latter was filtered off, washed twice with 50 ml of hexane and finally dried under a dynamic vacuum for 20 h. A stable solid was obtained.

Elemental analysis (C, H):

|  | C | H |
|---|---|---|
| Calcd.: | 52.11% | 9.23% |
| Found: | 52.3% | 8.7% |

$C_{18}H_{38}O_2Si_4$

M=414.840 g/Mol

NMR: (dmso-$d_6$)

$^1$H: δ=−0.11 ppm (s, 18H, SiCH$_3$); 0.32 ppm and 0.70 ppm (m, 6H in each case, SiCH$_2$); 5.27 ppm (s, 3H, SiOH); 7.35 ppm and 7.44 ppm (m, 5H, SiC$_6$H$_5$).

$^{13}$C{$^1$H}: δ=−0.43 ppm (s, SiCH$_3$); 2.52 ppm (s, Si(CH$_2$)$_4$); 9.91 ppm (s, Si(OH)CH$_2$); 127.85 ppm, 128.84 ppm, 134.19 ppm and 137.32 ppm (s, SiC$_6$H$_5$).

Example 7

Synthesis of $Si[(CH_2)_2Si(OH)Me_2]_4$ in tert.-butylmethylether 94.3 g (183.4 mmol) of $Si[(CH_2)_2SiClMe_2]_4$ were dissolved in 100 ml of diethyl ether and added drop-wise with vigorous stirring at room temperature to a solution of 110.3 ml (792.3 mmol) of triethylamine, 15.3 ml (850mmol) of water and 3 630 ml of tert.-butylmethylether. The triethylamine hydrochloride formed precipitated immediately as a white solid. The rate of the drop-wise addition was such that the reaction temperature lay between 25 ° C. and 30° C. On completion of the addition, stirring took place for a further hour and the precipitate was then filtered off through a frit. After the removal of the volatile components under vacuum at approx. 35° C., the crude product was obtained as a white solid. The latter was dissolved in as little thf as possible and dripped into 3 l of hexane with vigorous stirring. The fine, white precipitate so obtained was filtered off, washed once with hexane and then vacuum-dried.

The tert.-butylmethylether and the excess chlorodimethylsilane obtained after the above reaction was used for a second, similar reaction without further purification. The reaction course, as well as the quality of the fine product, remained unchanged.

General Instructions on the Manufacture of Coating Solutions

There were added to the carbosilane-dendrimers Si[(CH$_2$)$_2$Si(OH)Me$_2$]$_4$, Ph-Si[(CH$_2$)$_2$Si(OH)Me$_2$]$_3$ or Si[(CH$_2$)$_2$Si[(CH$_2$)$_2$Si(OH)Me$_2$]$_3$]$_4$, in the corresponding solvent, tetraethoxysilane (teos) and finally the catalyst formic acid. The reaction mixture was stirred until it was absolutely clear, and then stood until good processability was obtained. The exact test data for the manufacture of coating solutions 1 to 6 are listed in Table 1. The molar ratios, proportions by volume and concentrations of the substances used are listed in Table 2.

TABLE 1

Manufacture of coating solutions 1 to 6.

| Coating solution no. | Carbosilane-dendrimer Amount (mol) | TEOS Amount (mol) | Solvent Amount | HCOOH Amount | Water Amount | Time*) |
|---|---|---|---|---|---|---|
| 1 | Si[(CH$_2$)$_2$Si(OH)Me$_2$]$_4$ 500 mg (1.13 mmol) | 1 ml (4.49 mmol) | Isopropanol 1 ml | 0.44 ml | 0.06 ml | 40 min |
| 2 | Si[(CH$_2$)$_2$Si(OH)Me$_2$]$_4$ 200 mg (0.46 mmol) | 0.4 ml (1.8 mmol) | Isopropanol 0.5 ml | 0.03 ml | 0.1 ml | 70 min |

TABLE 1-continued

Manufacture of coating solutions 1 to 6.

| Coating solution no. | Carbosilane-dendrimer Amount (mol) | TEOS Amount (mol) | Solvent Amount | HCOOH Amount | Water Amount | Time*) |
|---|---|---|---|---|---|---|
| 3 | Si[(CH$_2$)$_2$Si(OH)Me$_2$]$_4$ 200 mg (0.46 mmol) | 0.4 ml (1.8 mmol) | Ethanol 0.5 ml | 0.03 ml | 0.1 ml | 75 min |
| 4 | Si[(CH$_2$)$_2$Si[(CH$_2$)$_2$Si(OH)Me$_2$]$_3$]$_4$ 1 g (0.67 mmol) | 1.8 ml (8.06 mmol) | Methanol 3 ml | 1.06 ml | 0.14 ml | — |
| 5 | Ph—Si[(CH$_2$)$_2$Si(OH)Me$_2$]$_3$ 200 mg (0.48 mmol) | 0.4 ml (1.8 mmol) | Ethanol 0.5 ml | 0.1 ml | 0.1 ml | 45 min |
| 6 | Ph—Si[(CH$_2$)$_2$Si(OH)Me$_2$]$_3$ 200 mg (0.48 mmol) | 0.32 ml (1.44 mmol) | Ethanol 0.5 ml | 0.1 ml | 0.1 ml | 45 min |

*)Time after which good processability has been obtained.

TABLE 2

Molar amounts and molar ratios of coating solutions 1 to 6.

| Coating solution no. | Carbosilane-dendrimer [mmol]/V**) | TEOS [mmol]/V**) | Solvent [mmol]/V**) | Water [mmol]/V**) | HCOOC [mmol]/V**) | Solids content*) |
|---|---|---|---|---|---|---|
| 1 | Si[(CH$_2$)$_2$Si(OH)Me$_2$]$_4$ 1.13/1 | 4.49/4 | Isopropanol 13.1/11.6 | 3.3/2.9 | 11.7/10.4 | 31% |
| 2 | Si[(CH$_2$)$_2$Si(OH)Me$_2$]$_4$ 0.46/1 | 1.80/4 | Isopropanol 6.6/14.4 | 5.6/12.1 | 0.8/1.7 | 30% |
| 3 | Si[(CH$_2$)$_2$Si(OH)Me$_2$]$_4$ 0.46/1 | 1.80/4 | Ethanol 6.6/18.7 | 5.6/12.2 | 0.8/1.7 | 30% |
| 4 | Si[(CH$_2$)$_2$Si[(CH$_2$)$_2$Si(OH)Me$_2$]$_3$]$_4$ 0.67/1 | 8.06/12 | Methanol 74.0/110.4 | 7.8/11.6 | 28.2/42.1 | 25% |
| 5 | Ph—Si[(CH$_2$)$_2$Si(OH)Me$_2$]$_3$ 0.48/1 | 1.80/3,8 | Ethanol 8.6/17.9 | 5.6/11.7 | 2.7/5.6 | 28% |
| 6 | Ph—Si[(CH$_2$)$_2$Si(OH)Me$_2$]$_3$ 0.48/1 | 1.44/3 | Ethanol 8.6/17.9 | 5.6/11.7 | 2.7/5.6 | 28% |

*)Carbosilane-dendrimer and SiO$_2$ in total solution.
**)Molar ratio of the components used, referred to carbosilan-dendrimer General Instructions on the Manufacture of Coating Films Prior to coating all the surfaces were cleaned carefully by rubbing with acetone. The approximate mount of the respective coating solution 1 to 6 required was then applied to the surface with a four-fold film casting frame of the company Erichsen, Model 360. The surfaces used had the following dimensions:

TABLE 3

Dimensions of the surfaces used

| | |
|---|---|
| Glass | 80 × 115 × 2.77 mm |
| Iron | 65 × 210 × 0.48 mm |
| Aluminium | 80 × 150 × 2.00 mm |
| Steel | 80 × 150 × 1.47 mm |
| Silicon | 114 × 114 × 0.38 mm |

The data on the nature of the surfaces, film thicknesses and drying conditions are given in Table 4. The results of the tests on the pencil hardness, the cross-cut adhesion test and the solvent resistance are contained in Table 5. Physical-chemical properties of films prepared from coating solution 1 are given in Table 6, while the mechanical properties of the coating film 1/5 are shown in Table 7.

TABLE 4

Manufacture of coating films from coating solutions 1, 2, 3, 5 and 6. (Coating solution 4 was cured in a plastics vessel to a moulding/film of 0.8 mm thickness).

| Coating solution film no. | Surface | Wet film thickness | Dry film thickness | Drying conditions |
|---|---|---|---|---|
| 1/1 | Glass | 120 µm | 27 µm | 24 h R.T. |
| 1/2 | Glass | 120 µm | 22 µm | 3 h R.T., 2 h 105° C., 19 h R.T. |
| 1/3 | Glass | 240 µm | 64 µm | 24 h R.T. |
| 1/4 | Glass | 240 µm | 33 µm | 3 h R.T., 2 h 105° C., 19 h R.T. |
| 1/5 | Iron | 120 µm | 9 µm | 24 h R.T. |
| 1/6 | Iron | 120 µm | 8 µm | 3 h R.T., 1 H 50° C., 4 h 80° C. |
| 1/7 | Iron | 120 µm | 10 µm | 24 h R.T., 2 h 105° C. |
| 1/8 | Iron | 240 µm | 38 µm | 24 h R.T. |
| 1/9 | Iron | 240 µm | 39 µm | 3 d 60° C., 2 h R.T. |
| 1/10 | Aluminium | 120 µm | 23 µm | 24 h R.T. |
| 1/11 | Aluminium | 120 µm | 19 µm | 17 h R.T., 2 h 105° C. |
| 1/12 | Steel | 120 µm | 18 µm | 24 h R.T. |
| 1/13 | Steel | 120 µm | 18 µm | 17 h R.T., 2 h 105° C. |
| 1/14 | Silicon | 120 µm | 4 µm | 24 h R.T. |
| 2/15 | Glass | 120 µm | 15 µm | 20 d R.T. |

TABLE 4-continued

Manufacture of coating films from coating solutions 1, 2, 3, 5 and 6. (Coating solution 4 was cured in a plastics vessel to a moulding/film of 0,8 mm thickness).

| Coating solution film no. | Surface | Wet film thickness | Dry film thickness | Drying conditions |
|---|---|---|---|---|
| 3/16 | Glass | 120 µm | 34 µm | 20 d R.T. |
| 5/17 | Glass | 120 µm | 10 µm | 15 d R.T. |
| 6/18 | Glass | 120 µm | 9 µm | 15 d R.T. |

TABLE 5

Preliminary tests on coating films 1 to 18.

| Coating film no. | Pencil hardness to ASTM D 3363 | Cross-cut adhesion test to ISO 2409 | Solvent resistance*) acetone, toluene, $CHCl_3$, ethanol, butylacetate, DMF |
|---|---|---|---|
| 1 | >5H | 0–1 | No change |
| 2 | >5H | 0–1 | No change |
| 3 | >5H | 0–1 | No change |
| 4 | >5H | 0–1 | No change |
| 5 | n.a. | 0–1 | No change |
| 6 | n.a. | 0–1 | No change |
| 7 | n.a. | 0–1 | No change |
| 8 | n.a. | 0–1 | No change |
| 9 | n.a. | 0–1 | No change |
| 10 | n.a. | 1 | No change |
| 11 | n.a. | 0–1 | No change |
| 12 | >5H | 0–1 | No change |
| 13 | >4H | 0–1 | No change |
| 14 | n.a. | 0–1 | No change |
| 15 | >5H | 0–1 | No change |
| 16 | >5H | 0–1 | No change |
| 17 | >5H | 0–1 | No change |
| 18 | >5H | 0–1 | No change |

*)Tested by five-minute rubbing of the coating films with a cotton-wool ball soaked in solvent or by dipping the surface in the solvent.
n.a. = Test not applicable on rough or soft surfaces (used iron and aluminium plates)

TABLE 6

Physical-chemical properties of coating films of coating solution 1.

| | Coating films of coating solution 1 |
|---|---|
| Roughness, $R_A$ value | 31 nm +/− 5 nm |
| Roughness, $R_A$ value (after cleaning) | 21 nm +/− 4 nm |
| Surface tension | 28.5 mN/m |
| Surface tension (after cleaning) | 28.7 mN/m |
| Heat resistance (air) | 210–230° C.*) |
| Heat resistance ($N_2$) | 490° C.*) |
| Absorbance in the UV/visual range | |
| 360 to 560 nm | <0.002 |
| 560 to 810 nm | ≦0.03 |
| Refractive index (λ = 633 nm) | 1,4642 +/− 0.0002 |

*)From TGA, i.e. decomposition of the organic component occurs above this temperature.

TABLE 7

Mechanical properties of coating film 1/5.

| Indentation test to ISO 1520 | 11 mm |
|---|---|
| Ball impact test to ASTM D 2794-93 | 20 inch-pound |

Example 8

Treatment of Activated Carbon in Powder Form with $H_2PtCl_6$ (Cat I)

49.5 g of activated carbon Norit CN 1 were suspended in 300 ml of double-distilled water and mixed with 200 ml of an aqueous $H_2PtCl_6$ solution containing 0.5 g Pt calculated as metal. Stirring took place for 10 minutes and the catalyst was then extracted on a nutsch filter. The water-moist crude product (153 g) was dried at 0.1 Pa and 110° C. and stored under argon. The catalyst Cat I contained 1% Pt.

Example 9

Treatment of Lumpy Activated Carbon with $H_2PtCl_6$ (Cat II)

49.5 g (=114.6 ml) of activated carbon extrudate Norit ROX 0.8 were soaked with 33.9 ml of an aqueous $H_2PtCl_6$ solution containing 0.5 g Pt calculated as metal. The crude product was first of all dried in a nitrogen current at 110° C., then dried at 0.1 Pa and 110° C. and stored under argon. The catalyst contained 1% Pt.

Example 10

Treatment of $SiO_2$ with $H_2PtCl_6$ (Cat III)

49.5 g of $SiO_2$ (Merck 657) were made into a paste with 132 ml of an aqueous $H_2PtCl_6$ solution containing 0.5 g Pt calculated as metal. The water-moist crude product was first of all dried in a drying cabinet at 110° C., then dried at 0.1 Pa and 110° C. and stored under argon. The catalyst contained 1% Pt.

Example 11

Treatment of $Al_2O_3$ in Powder Form with $H_2PtCl_6$ (Cat IV)

49.5 g of γ-$Al_2O_3$ (Rhone-Poulenc, SPH 509). were made into a paste with 40 ml of an aqueous $H_2PtCl_6$ solution containing 0.5 g Pt calculated as metal. The water-moist crude product was first of all dried in a drying cabinet at 110° C., then dried at 0.1 Pa and 110° C. and stored under argon. The catalyst contained 1% Pt.

Example 12

Treatment of $TiO_2$ in Powder Form with $H_2PtCl_6$ (Cat V)

49.5 g of $TiO_2$ (Bayer) were made into a paste with 70 ml of an $H_2PtCl_6$ containing 0.5 g Pt calculated as metal. The water-moist crude product was first of all dried in a drying cabinet at 110° C., then dried at 0.1 Pa and 110° C. and stored under argon. The catalyst contained 1% Pt.

Example 13

Synthesis of $Si[(CH_2)_2SiClMe_2]_4$ with 5g of Cat I 867 g (9.17 mol) of chlorodimethylsilane and 5 g of the dried catalyst Cat I were added to 250 g (1.84 mol) of tetravinylsilane in 600 ml of thf. Heating took place with vigorous stirring until the clearly exothermal reaction started after a few minutes and the external heat source was then removed. The reaction supported itself for approx. 30 min under vigorous reflux. When the reflux became weaker, heating took place for a further 15 h to 55° to 60° C., followed by cooling to room temperature. The supported catalyst was filtered off through a frit. From the colourless solution all the volatiles were removed in vacuo. In so doing the product crystallized out spontaneously as a colourless solid. The latter was then vacuum-dried for a further 20 h.

Yield: 861.5 g corresponding to 92% of theoretical.

Example 14

Synthesis of $Si[(CH_2)_2SiClMe_2]_4$ with 4 g of Cat I

The reaction took place similarly to Example 2, but with only 4 g of the supported catalyst Cat I. The mixture of thf and surplus chlorodimethylsilane condensed out after the filtration was used again in Example 3.

Yield: 854.3 g corresponding to 91% of theoretical.

Example 15

Synthesis of $Si[(CH_2)_2SiClMe_2]_4$ with 4 g of Cat I 729 g (7.71 mol) of chlorodimethylsilane and 4 g of the dried catalyst Cat I were added to 250 g (1.84 mol) of tetravinylsilane and to the condensate from Example 3 consisting of thf and chlorodimethylsilane. The whole was heated under vigorous stirring to approx. 40° C. until the clearly exothermal reaction started after a few minutes and the external heat source was then removed. The reaction supported itself for approx. 60 min under vigorous reflux. When the reflux became weaker, heating took place for a further 15 h to 55° to 60° C., followed by cooling to room temperature. The supported catalyst was then filtered off through a frit and from the colourless solution all the volatiles were removed in vacuo. In so doing the product crystallized out spontaneously as a colourless solid. The latter was then vacuum-dried for a further 20 h.

Yield: 849.0 g corresponding to 90% of theoretical.

Example 16

Synthesis of $Si[(CH_2)_2SiClMe_2]_4$ with Cat II 34.7 g (366.7 mmol) of chlorodimethylsilane and 200 mg of the supported catalyst Cat II were added to 10 g (73.3 mmol) of tetravinylsilane in 30 ml of thf. The reaction mixture was heated to 40° C. and the external heat source removed after the start of the exothermal reaction. The temperature then rose spontaneously to approx. 60° C.; on completion of the exothermal reaction, heating for a further 15 h to 40° C. took place, followed by cooling to room temperature. The catalyst was filtered off and the colourless solution freed from volatile components in vacuo. The product was obtained as a white solid.

Yield: 32.5 g corresponding to 86% of theoretical.

Example 17

Synthesis of $Si[(CH_2)_2SiClMe_2]_4$ with Cat III 34.7 g (366.7 mmol) of chlorodimethylsilane and 200 mg of the supported catalyst Cat III were added to 10 g (73.3 mmol) of tetravinylsilane in 30 ml of thf. The reaction mixture was heated to 40° C. and the external heat source removed after the start of the exothermal reaction. The temperature then rose spontaneously to approx. 65° C.; on completion of the exothermal reaction, heating for a further 2 h to 50° C. took place, followed by cooling to room temperature. The catalyst was filtered off and the colourless solution freed from volatile components in vacuo. The product was obtained as a white solid.

Yield: 34.6 g corresponding to 92% of theoretical.

Example 18

Synthesis of $Si[(CH_2)_2SiClMe_2]_4$ with Cat IV 86.8 g (917.0 mmol) of chlorodimethylsilane and 0.5 g of the catalyst Cat IV were added to 25 g (183.4 mmol) of tetravinylsilane in 60 ml of thf. Heating took place slowly to 40° C., and after about 30 min a strongly exothermal reaction started. In so doing the reaction mixture heated up to 65° C. and had to be cooled in the meantime with a cooling bath (acetone/dry ice). After the end of the exothermal reaction heating took place for a further 2 h to 50° C., followed by stirring for a further 20 h at room temperature. The catalyst was then filtered off through a frit and the filtrate freed of volatile components in vacuo.

Yield: 80.8 g corresponding to 86% of theoretical.

Example 19

Synthesis of $Si[(CH_2)_2SiClMe_2]_4$ with Cat V 86.8 g (917.0 mmol) of chlorodimethylsilane and 0.2 g of the catalyst Cat V were added to 25 g (183.4 mmol) of tetravinylsilane in 60 ml of thf. Heating took place slowly to 40° C. and the external heat source was removed as soon as the exothermal reaction started. In so doing the reaction mixture heated up rapidly to 60° C. After the end of the exothermal reaction heating took place for a further 2 h to 50° C., followed by stirring for a further 20 h at room temperature. The catalyst was then filtered off through a frit and the filtrate freed of volatile components in vacuo.

Yield: 70 g corresponding to 74% of theoretical.

Example 20

Synthesis of $Si[(CH_2)_2SiClMe_2]_4$ with Cat I in tert.-butylmethylether 509 ml (433.7 g; 4.59 mol) of chlorodimethylsilane and 2 g of the catalyst Cat I were added to 125 g (0.92 mol) of tetravinylsilane in 300 ml of tert.-butylmethylether. Heating took place to 40°–45° C. and the external heat source was removed as soon as the exothermal reaction started. The temperature rose slowly to 55° C. due to the consumption of the low boiler (chlorodimethylsilane) and dropped again after about 30 min with the end of the exothermal reaction. Heating then took place for a further 2 h to 50° C., followed by cooling to room temperature and removal of the catalyst by filtration through a frit. (Product crystallized in the frit was easily transferred by heating with a hair-drier). The colourless filtrate was freed of volatile components in vacuo and the product was obtained as colourless crystals.

Yield: 435 g corresponding to 92% of theoretical.

What is claimed is:

1. Functional carbosilane-dendrimers with the general formula

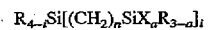

with i=3,4, n=2–6 and R=alkyl and/or aryl, where n can be the same or different inside the molecule and where the other groups stand for the following a) X=OH with a=1 or b) X=[(CH$_2$)$_n$Si(OH)R$_2$]

with a=1 to 3 or c) X=[(CH$_2$)$_n$SiR$_{3-a}$[(CH$_2$)$_n$Si(OH)R$_2$]$_a$]

with a=1 to 3 or d) X=[(CH$_2$)$_n$SiR$_{3-a}$[(CH$_2$)$_n$SiR$_{3-a}$[(CH$_2$)$_n$Si(OH)R$_2$]$_a$]$_a$]

with a=1 to 3.

2. Functional carbosilane-dendrimers according to claim 1, characterised in that the values of the indices n inside the molecule are the same.

3. Method for manufacturing the carbosilane-dendrimers according to claim 1, characterised in that dendrimers with the formula $$R_{4-i}[Si(CH_2)_nSiZ_cR_{3-c}]_i$$

with i=3,4, n=2 to 6 and R=alkyl and/or aryl, where n can be the same or different inside the molecule and where the other groups stand for the following:

a) Z=Cl, Br, I, or OR with c=1, or b) Z=[(CH$_2$)$_n$SiWR$_2$]

with c=1 to 3 and W stands for Cl, Br, I or OR or c) Z=[(CH$_2$)$_n$SiR$_{3-c}$[(CH$_2$)$_n$SiWR$_2$]$_c$]

with c=1 to 3, W stands for Cl, Br, I or OR or d) Z=[(CH$_2$)$_n$SiR$_{3-c}$[(CH$_2$)$_n$SiR$_{3-c}$[(CH$_2$)$_n$SiWR$_2$]$_c$]$_c$]

with c=1 to 3, W stands for Cl, Br, I or OR are hydrolysed in a non-polar solvent with water in the presence of a base.

4. Method for manufacturing carbosilane-dendrimers according to claim 3, characterised in that triorganic mines are used as said base.

5. Method for manufacturing carbosilane-dendrimers according to claim 1, characterised in that aliphatic ethers are used as the non-polar solvent.

6. Method for manufacturing compounds with the formula $$R_{4-i}Si[(CH_2)_pSiZ_eR_{3-e}]_i$$

with p=2–10, e=1–3, i=3, 4 and R=alkyl and/or aryl, where n can be the same or different inside the molecule and where the other groups stand for the following:

a) Z=halogen, or OR or b) Z=[(CH$_2$)$_p$SiW$_e$R$_{3-e}$] with W=halogen, or OR or c) Z=[(CH$_2$)$_p$SiR$_{3-e}$[(CH$_2$)$_p$SiW$_e$R$_{3-e}$]$_e$]

with W=halogen, or OR, characterised in that alkenyl-silanes with the formula $$R_{4-i}Si[(CH_2)_{p-2}Q]_i$$

with p=2–10, i=3, 4, R=alkyl and/or aryl and a) Q=C$_2$H$_3$ or b) Q=[(CH$_2$)$_p$Si(C$_2$H$_3$)$_e$R$_{3-e}$] with e=1–3 or c) Q=[(CH$_2$)$_p$SiR$_{3-e}$[(CH$_2$)$_p$Si(C$_2$H$_3$)$_e$R$_{3-e}$]$_e$] with e=1–3 are reacted with hydridosilanes of the formula $$HSiP_eR_{3-e}$$

with e=1–3, P=halogen, or OR and R=alkyl and/or aryl in the presence of heterogeneous catalysts.

7. Method according to claim 6, characterised in that there is used as a heterogeneous catalyst a catalyst which contains platinum or a platinum compound as the catalytically active component and said platinum or platinum compound is supported on a carbon support material.

8. Method according to claim 7, characterised in that hexachloroplatinic acid supported on activated carbon is used as the heterogeneous catalyst.

9. Method according to claim 6, characterised in that the reaction takes place discontinuously in a solvent.

10. Method according to claim 6, characterised in that tetravinylsilane is used as the alkenylsilane and HSiClMe$_2$, where Me is a methyl group, as the hydridosilane.

11. Organic-inorganic hybrid materials that are obtained by reacting carbosilane-dendrimers with the formula $$R_{4-i}Si[(CH_2)_nSiX_aR_{3-a}]_i$$

with i=3,4, n=2–6 and R=alkyl and/or aryl, where n can be the same or different inside the molecule and where the other groups stand for the following:

a) X=OH with a=1 or b) X=[(CH$_2$)$_n$Si(OH)R$_2$]

with a=1 to 3, or c) X=[(CH$_2$)$_n$SiR$_{3-a}$[(CH$_2$)$_n$Si(OH)R$_2$]$_a$]

with a=1–3, or d) X=[(CH$_2$)$_n$SiR$_{3-a}$[(CH$_2$)$_n$SiR$_{3-a}$[(CH$_2$)$_n$Si(OH)R$_2$]$_a$]$_a$]

with a=1–3, with metal alkoxides of the formula $$M(OR')_x$$

with M=Si, Ge, Sn, B, Al, Ga, In, Ti, Zr, Hf, V, Nb or Ta, R'=an unbranched or branched C$_1$–C$_5$ alkyl group and x, depending on the oxidation number of M, stands for 3 or 4, with water and in the presence of a catalyst selected from the group consisting of an organometallic compound, an organic acid and an inorganic acid.

12. Method for manufacturing coatings, characterised in that carbosilane-dendrimers with the formula $$R_{4-i}Si[(CH_2)_nSiX_aR_{3-a}]_i$$

with i=3,4, n=2–6 and R=alkyl and/or aryl, where n can be the same or different inside the molecule and where the other groups stand for the following:

a) X=OH with a=1 or b) X=[(CH$_2$)$_n$Si(OH)R$_2$]

with a=1 to 3 or c) X=[(CH$_2$)$_n$SiR$_{3-a}$[(CH$_2$)$_n$Si(OH)R$_2$]$_a$]

with a=1–3, or d) X=[(CH$_2$)$_n$SiR$_{3-a}$[(CH$_2$)$_n$SiR$_{3-a}$[(CH$_2$)$_n$Si(OH)R$_2$]$_a$]$_a$]

with a=1–3, are reacted with metal alkoxides of the formula $$M(OR')_x$$

with M=Si, Ge, Sn, B, Al, Ga, In, Ti, Zr, Hf, V, Nb, or Ta, R'=an unbranched or branched C$_1$–C$_5$ alkyl group and x, depending on the oxidation number of M, stands for 3 or 4, with water and in the presence of a catalyst selected from the group consisting of an organometallic compound, an organic acid and an inorganic acid and optionally a solvent.

13. A method of using carbosilane-dendrimers according to claim 1, wherein catalytically active metal compounds having the formula MX, where M=a metal and X=alkyl, alkoxy, halogeno or hydrido, are reacted with the carbosilane-dendrimers so as to form compounds wherein the catalytically active metal M is bonded to said carbosilane-dendrimers.

14. A method of using the organic-inorganic hybrid materials according to claim 11, wherein said hybrid materials are painted on a surface of a material to form a protective coating.

15. A method according to claim 12, wherein X=OH and a=1.

16. Organic-inorganic hybrid materials according to claim 11, wherein said organometallic compound is zinc octoate.

17. Method for manufacturing coatings according to claim 12, wherein said organometallic compound is zinc octoate.

* * * * *